US009596875B2

(12) United States Patent
Hoshi et al.

(10) Patent No.: US 9,596,875 B2
(45) Date of Patent: Mar. 21, 2017

(54) FERMENTED FOOD CONTAINING BIFIDOBACTERIUM BACTERIA AND METHOD FOR PRODUCING THE SAME

(75) Inventors: Ryotaro Hoshi, Minato-ku (JP); Nobuhiro Ogasawara, Minato-ku (JP); Masaki Yoshikawa, Minato-ku (JP); Tatsuyuki Kudo, Minato-ku (JP); Ryoichi Akahoshi, Minato-ku (JP); Susumu Mizusawa, Minato-ku (JP); Haruyuki Kimizuka, Chuo-ku (JP); Takao Suzuki, Chuo-ku (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 880 days.

(21) Appl. No.: 11/916,191

(22) PCT Filed: May 22, 2006

(86) PCT No.: PCT/JP2006/310124
§ 371 (c)(1),
(2), (4) Date: Nov. 30, 2007

(87) PCT Pub. No.: WO2006/129508
PCT Pub. Date: Dec. 7, 2006

(65) Prior Publication Data
US 2010/0015281 A1 Jan. 21, 2010

(30) Foreign Application Priority Data

Jun. 2, 2005 (JP) .................................. 2005-162226
Aug. 12, 2005 (JP) .................................. 2005-234748

(51) Int. Cl.
| | | |
|---|---|---|
| A23L 1/00 | (2006.01) | |
| A23L 1/30 | (2006.01) | |
| A23L 1/28 | (2006.01) | |
| A23C 9/12 | (2006.01) | |
| A23C 9/123 | (2006.01) | |
| A23C 9/13 | (2006.01) | |
| A23L 1/10 | (2006.01) | |
| A23L 1/212 | (2006.01) | |
| A61K 8/02 | (2006.01) | |
| A61K 8/97 | (2006.01) | |
| A61K 8/99 | (2006.01) | |
| A61Q 19/08 | (2006.01) | |

(52) U.S. Cl.
CPC .......... *A23L 1/3002* (2013.01); *A23C 9/1234* (2013.01); *A23C 9/13* (2013.01); *A23L 1/1016* (2013.01); *A23L 1/212* (2013.01); *A23L 1/3014* (2013.01); *A61K 8/02* (2013.01); *A61K 8/97* (2013.01); *A61K 8/99* (2013.01); *A61Q 19/08* (2013.01); *A23V 2002/00* (2013.01); *A23Y 2300/00* (2013.01); *A61K 2800/92* (2013.01)

(58) Field of Classification Search
CPC ........ A23V 2002/00; A23V 2200/3204; A23V 2200/32; A23V 2200/30; A23V 2200/00; A23C 9/1234; A23C 9/123; A23C 9/12; A23C 9/00; A23C 9/1307; A23C 9/13; A23L 1/1016; A23L 1/212; A23L 1/3002; A23L 1/3014; A23Y 2300/00; A61K 2800/92; A61K 8/02; A61K 8/97; A61K 8/99; A61Q 19/08
USPC ..................................... 426/43, 61, 7, 34, 42
See application file for complete search history.

(56) References Cited

U.S. PATENT DOCUMENTS

| | | | | |
|---|---|---|---|---|
| 3,677,897 | A | * 7/1972 | Jeffreys ..................... | 435/252.4 |
| 7,115,291 | B1 | * 10/2006 | Kuma et al. .................... | 426/43 |
| 2007/0082102 | A1 | * 4/2007 | Magomet et al. ............ | 426/548 |
| 2010/0166679 | A1 | * 7/2010 | Abelyan et al. ................ | 424/49 |
| 2011/0293538 | A1 | * 12/2011 | Ley et al. ....................... | 424/49 |

FOREIGN PATENT DOCUMENTS

| | | |
|---|---|---|
| CN | 1377231 A | 10/2002 |
| CN | 1483332 A | 3/2004 |
| JP | 57-4291 | 1/1982 |
| JP | 57-004291 | 1/1982 |
| JP | 63-192367 | 8/1988 |
| JP | 2-42962 | 2/1990 |
| JP | 4-248971 | 9/1992 |
| JP | 4-248972 | 9/1992 |
| JP | 06-253734 | 9/1994 |

(Continued)

OTHER PUBLICATIONS

Chen, M-j, et al., Optimization of the viability of probiotics in fermented milk drink by the response surface method. Asian-Aust. J. Anim. Sci., 17(5) (2004) 705-711.*

(Continued)

*Primary Examiner* — Hamid R Badr
(74) *Attorney, Agent, or Firm* — Oblon, McClelland, Maier & Neustadt, L.L.P.

(57) ABSTRACT

Provided is a fermented food containing an extract of at least one plant material selected from the group consisting of turmeric, *Houttuynia cordata* Thunb., *Eucommia ulmoides* Oliv., rice bran, persimmon leaves, *perilla*, clove, cinnamon and *Rubus suavissimus* S. Lee (Rosaceae) and bacteria of the genus *Bifidobacterium*. The fermented food contains an excellent and novel material with which the viability of the bacteria of the genus *Bifidobacterium* can be improved in storage of the product, and even when used in products such as beverages or foods, does not deteriorate the flavor of the product, thereby the bacteria of the genus *Bifidobacterium* can be contained at high concentration which provides various physiological effects.

22 Claims, No Drawings

(56) References Cited

FOREIGN PATENT DOCUMENTS

| | | | | |
|---|---|---|---|---|
| JP | 7-170933 | | 7/1995 | |
| JP | 7-227207 A | | 8/1995 | |
| JP | 2577692 | | 11/1996 | |
| JP | 9-163977 | | 6/1997 | |
| JP | 11-113484 | | 4/1999 | |
| JP | 11-266824 | | 10/1999 | |
| JP | 2000-83654 | | 3/2000 | |
| JP | 2000-083654 | * | 3/2000 | ............... A23L 1/30 |
| JP | 2001-178403 | | 7/2001 | |
| JP | 2001-178410 | | 7/2001 | |
| JP | 2001-190251 | | 7/2001 | |
| JP | 2001-190252 | | 7/2001 | |
| JP | 2001-190272 | | 7/2001 | |
| JP | 2001-238593 | | 9/2001 | |
| JP | 2001-352940 | | 12/2001 | |
| JP | 3261571 | | 12/2001 | |
| JP | 2002-65199 | | 3/2002 | |
| JP | 2003-88343 | | 3/2003 | |
| JP | 2003-250528 | | 9/2003 | |
| JP | 2003-265151 | | 9/2003 | |
| JP | 2003-289797 | | 10/2003 | |
| JP | 2004-222652 | | 8/2004 | |
| JP | 2004-345986 | | 12/2004 | |
| JP | 2005-58132 | | 3/2005 | |
| JP | 2005-58133 | | 3/2005 | |
| KR | 10-0150395 | * | 7/1995 | ............... A23L 2/38 |
| WO | WO 01/10233 A1 | | 2/2001 | |

OTHER PUBLICATIONS

Office Action issued on Dec. 7, 2011 in the corresponding Chinese Patent Application No. 200680018908.9 (English Translation only).

J.S. Yun et al., "Fermentative production of DL-lactic acid from amylase-treated wheat and rice brans hydrolyzate by a novel lactic acid bacterium, *Lactobacillus* sp.", Biotechnology Letter 5, vol. 26, No. 20, pp. 1613-1616. (2004).

Sanae Okada et al., "Biseibutsu ni yoru nipponsan hakkocha, awabancha/goishicha/kurocha no chosa", Nogakushuho, vol. 27, No. 3, pp. 269-276. (1983).

Kazuo Ooishi et al., "Development of New Fermented Tea-Drink Using Microorganisms" Shizuoka-ken Kogyo Gijutsu Center Kenkyu Hokoku, No. 33, pp. 101-108. (1988).

Toshiaki Kobayashi, "Reports of the Shizuoka Prefectural Industrial Technology Center", Cha, vol. 42, No. 2, pp. 16-19 (1989).

Notice of Preliminary Rejection as received in the corresponding Korean Patent Application No. 10-2007-7029528 dated Oct. 18, 2012.

Combined Chinese Office Action and Search Report issued Dec. 16, 2013 in Patent Application No. 201210025188.6 (with English language translation).

Yang Jiam Huang Friendship, "China Special Tea," China Agriculture Press, First Edition, Jul. 30, 2004, 4 Pages.

Extended European Search Report issued Mar. 2, 2015 in Patent Application No. 06756430.2.

Office Action issued Jan. 26, 2011 in connection with corresponding Japanese Application No. 2007-518915, filed Jul. 12, 2007.

English translation of International Preliminary Report on Patentability issued Mar. 27, 2008 in corresponding International Application No. PCT/JP2006/310123, filed May 22, 2006.

N. Sugano et al., "Komenuka to nyu o genzairyo to shita hakko shokuhin no kaihatsu ni kansuru kenkyu", Reports of Kochi Prefectural Industrial Technology Center, vol. 32, pp. 21-29. (2001).

Satsuki Hasekura, "Nukamisozuke ni kansuru kenkyu" Journal of Home Economics of Japan, vol. 28, No. 1, pp. 1-14. (1977).

* cited by examiner

FERMENTED FOOD CONTAINING BIFIDOBACTERIUM BACTERIA AND METHOD FOR PRODUCING THE SAME

TECHNICAL FIELD

The present invention relates to fermented foods including bacteria of the genus *Bifidobacterium*, and more specifically to fermented foods, which contain viable bacteria of the genus *Bifidobacterium* at high concentration, and also to a method of preparing such fermented foods.

BACKGROUND ART

Bacteria of the genus *Bifidobacterium* are clearly known to have various effects such as improving intestinal flora, improving bowel movement, improving intestinal function, preventing infection, immunostimulation and preventing cancers likewise lactic acid bacteria represented by bacteria of the genus *Lactobacillus* and the like. These microorganisms are considered to improve intestinal environment, thus contributing to human health.

To obtain the above-described effects with bacteria of the genus *Bifidobacterium*, it is required to maintain a large number of the viable cell count of the bacteria within products such as fermented milks. Since, however, the bacteria of the genus *Bifidobacterium* are generally anaerobic bacteria, they are poor in viability, and die rapidly especially under the presence of oxygen.

There are, therefore, proposed methods for enhancing the viability of bacteria of the genus *Bifidobacterium* in products such as fermented milks prepared by making use of the bacteria. Examples of the methods include those making use of sucrose or sorbitol (D-glucitol) (Patent Document 1), erythritol (Patent Document 2) and lactitol (Patent Document 3).

Further, to provide bacteria of the genus *Bifidobacterium* in their active state for the consumers, measures are being taken such as putting fermentation products containing bacteria of the genus *Bifidobacterium* immediately after preparation in a container made of an oxygen-impermeable material to completely block the oxygen from coming into contact with the products. In this method, however, the use of oxygen-impermeable container involves many problems in terms of disposal and cost, and thus, the usability of the container is limited.

Therefore, studies are being made on methods of maintaining the viability of bacteria of the genus *Bifidobacterium* even under aerobic conditions and several methods have been reported. Specifically, there has been reported a method making use of N-acetylglucosamine, panthotenic acid, panthetine, pantetheine, peptides and lactulose. In this method, however, the materials used are themselves relatively high in costs, and when they are used in foods, the flavor and taste of the foods is profoundly affected. Therefore, taking into consideration the effects for the viability of the bacteria as well, there has been a desire for a more convenient material.

It is considered that the viability of bacteria of the genus *Bifidobacterium* is influenced by the strains used, pH of products (beverages, foods and the like), sugars added as a sweetener, the amount of dissolved oxygen and the like. In order to improve this, considerations are being made on addition of yeast or lactic acid bacteria, combined use of vitamin C, the material of the product container and the like. However, to meet the consumer preference that is becoming diversified recently and the requirement to further improve the viability of the bacteria, there is a desire for a material which can be used for viability improvement.

[Patent Document 1] JP-A-57-004291
[Patent Document 2] JP-B-2577692
[Patent Document 3] JP-B-3261571

DISCLOSURE OF THE INVENTION

Problems to be Solved by the Invention

An object of the present invention is, therefore, to find an excellent and novel material with the use of which various physiological effects can be obtained while maintaining the viability of bacteria of the genus *Bifidobacterium* in storage of a product such as a beverage or food containing the bacteria without developing problems in the flavor of the product, and to use the material for provision of a fermented food containing viable bacteria of the genus *Bifidobacterium* at high concentration, the viability of the bacteria being improved with the use of the material. Another object of the present invention is to provide, in preparation of a fermented food containing bacteria of the genus *Bifidobacterium*, a method for improving the viability of the bacteria in storage of the fermented food.

Means for the Solving the Problems

To achieve the above-described objects, the present inventors have conducted extensive research. As a result, it has been found that by adding an extract extracted from a specific plant, the viable cell count of bacteria of the genus *Bifidobacterium* contained in a fermented food can be stably maintained even after storage of the food, leading to the completion of the present invention.

In one aspect of the present invention, there is thus provided a fermented food comprising an extract of at least one plant material selected from the group consisting of turmeric, *Houttuynia cordata* Thunb., *Eucommia ulmoides* Oliv., rice bran, persimmon leaves, *perilla*, clove, cinnamon and *Rubus suavissimus* S. Lee (Rosaceae) and bacteria of the genus *Bifidobacterium*.

In another aspect of the present invention, there is also provided a fermented food comprising an extract of at least one plant material selected from the group consisting of turmeric, *Houttuynia cordata* Thunb., *Eucommia ulmoides* Oliv., rice bran, persimmon leaves, *perilla*, clove, cinnamon and *Rubus suavissimus* S. Lee (Rosaceae) and bacteria of the genus *Bifidobacterium*, the extract being obtained by acid extraction preferably under an acidic condition not higher than pH 4.0.

In a further aspect of the present invention, there is also provided a method for preparing a fermented food comprising bacteria of the genus *Bifidobacterium*, which comprises adding an extract of at least one plant material selected from the group consisting of turmeric, *Houttuynia cordata* Thunb., *Eucommia ulmoides* Oliv., rice bran, persimmon leaves, *perilla*, clove, cinnamon and *Rubus suavissimus* S. Lee (Rosaceae) at an arbitrary stage.

In a still further aspect of the present invention, there is also provided a method for improving viability of bacteria of the genus *Bifidobacterium*, comprising adding an extract of at least one plant material selected from the group consisting of turmeric, *Houttuynia cordata* Thunb., *Eucommia ulmoides* Oliv., rice bran, persimmon leaves, *perilla*, clove, cinnamon and *Rubus suavissimus* S. Lee (Rosaceae).

The extracts contained in the fermented foods of the present invention and have been derived from at least one plant material selected from the group consisting of turmeric, *Houttuynia cordata* Thunb., *Eucommia ulmoides* Oliv., rice bran, persimmon leaves, *perilla*, clove, cinnamon and *Rubus suavissimus* S. Lee (Rosaceae), provide excellent viability-improving effects for the bacteria of the genus *Bifidobacterium* and moreover, have practically no effect on the flavor. A fermented food of the present invention, which is obtained by the use of the extract, therefore has satisfactory flavor without undergoing much decrease in the viable cell count of the bacteria even after storage of the food for a long period of time, and is excellent for the promotion of health.

BEST MODE FOR CARRYING OUT THE INVENTION

The fermented food of the present invention contains an extract of at least one plant material selected from the group consisting turmeric, *Houttuynia cordata* Thunb., *Eucommia ulmoides* Oliv., rice bran, persimmon leaves, *perilla*, clove, cinnamon and *Rubus suavissimus* S. Lee (Rosaceae) (hereinafter, it may be simply called to as "an extract").

Among the plant materials which can each be used as a raw material for the above-mentioned extract, turmeric is the rootstock of *Curcuma longa* L. or *Curcuma aromatica* Salisb. In the present invention, *Curcuma longa* L. is particularly preferred among plants belonging to Curcuma. *Curcuma longa* L. is known to have effects such as hepatic function improving effects, hangover preventing effects, gastric antisecretory effects and gastrointestinal disfunction improving effects.

*Houttuynia cordata* Thunb. is a plant belonging to *Houttuynia cordata*. To obtain an extract from *Houttuynia cordata* Thunb., aerial grass parts and branch parts can be used, with the use of grass parts being particularly preferred. *Houttuynia cordata* Thunb. is known to have muscosal inflammation suppressing effects.

*Eucommia ulmoides* Oliv. is a plant belonging to *Eucommia ulmoides*. To obtain an extract from *Eucommia ulmoides* Oliv., leaves and branches can be used, with the use of leaves being particularly preferred. *Eucommia ulmoides* Oliv. is known to have effects such as blood pressure control, stress relief and prevention of lifestyle-related diseases.

Rice bran is a mixture of perocarps, aleurone layers and germs of kernels (brown rice) available from *Oryza Sativa* without the chaff paddy. This rice bran is known to have effects such as immunity enhancement, fatty liver prevention and the like.

Persimmon leaves include leaves of the plant of *Diospyros Kaki* Thunb., *Diospyros lotus* L., or *Diopyros lotus* L. var. *glabra Makino*. In the present invention, *Diospyros Kaki* Thunb. are particularly preferred among the plants of the genus *Diospyros* because the leaves are known to have effects such as suppressing sneezing, nasal congestion, runny nose and the like.

*Perilla* includes *Perilla frustescens* (L.) *Britton* var. acuta *Kudo, Perilla frustescens* (L.) *Britton* var. acuta *Kudo* forma viridis *Makino, Perilla frustescens* (L.) *Britton* var. crispa (Thunb) Decne. In the present invention, *Perilla frustescens* (L.) *Britton* var. acuta *Kudo* is particularly preferred. To obtain an extract from *perilla*, leaves, branches and seeds can be used, with the use of leaves being particularly preferred. *Perilla* is known to have effects such as antiallergic effects, hypoglycemic effects and skin rejuvenation.

Clove is the bud of *Syzygium aromaticum* (L.) Merr. et Perry or *Eugenia caryophyllata* Thunb. Clove is known to have preservation effects, uterine contraction activities, dental pain reduction effects, and the like.

Cinnamon is the bark of *Cinnamomum zeylanicum* Nees or *Cinnamomum cassia* Blume. *Cinnamomum zeylanicum* Nees is particularly preferred among these *cinnamomum* plants. Cinnamon is known to have effects such as antibacterial activities, body-warming effects, antipyretic effects, digestive system activation effects, amelioration effects for various cold symptoms, indigestion relief, diarrhea relief and nausea relief.

*Rubus sauvissimus* S. Lee (Rosaceae) is a plant belonging to *Rubus*. To obtain an extract from *Rubus sauvissimus* S. Lee (Rosaceae), its leaves and stem can be used, with the use of its leaves being particularly preferred. *Rubus sauvissimus* S. Lee (Rosaceae) is attracting attention in recent years for its anti-inflammatory activities and antiallergic effects.

To obtain an extract from one or more of the above-described plant materials, it is only necessary to extract with a solvent the plant material or materials either as they are or after optionally applying processings such as washing, peeling, drying and/or crushing. Such extracts may be used either singly or in combination. A mixed extract may also be used, which is obtained by mixing a plurality of plant materials and extracting them. Among these extracts, preferred are an extract from persimmon leaves and an extract from *Rubus sauvissimus* S. Lee (Rosaceae).

Solvents usable in preparation of the extracts include water and organic solvents such as lower alcohols having 1 to 5 carbon atoms, e.g., ethanol, ethyl acetate, glycerol and propylene glycol. Two or more of these solvents may be used together as a mixed solvent. Among these solvents, water and aqueous solvents such as water-lower alcohols are particularly preferred.

No particular limitation is imposed on the extraction method making use of the above-mentioned solvent, but acid extraction is preferred as it can efficiently extract from the plant material or materials components which enhance the viability of bacteria of the genus *Bifidobacterium* and can also bring about sufficient effects even when the extract is added in a small amount. Acid extraction can preferably be performed under an acidic condition of pH 4.0 or lower, especially pH 3.0 to 4.0. No particular limitation is imposed on acid ingredient adapted to regulate the pH of the solvent in this acid extraction, and any ingredient can be used insofar as it is acidic. Among such acid ingredients, preferred are organic acids such as citric acid, malic acid, tartaric acid, succinic acid, lactic acid and acetic acid.

Furthermore, extraction conditions for the extract with the use of the above-mentioned solvent are not particularly limited, and the extraction processing can be carried out, for example, by treatment for 30 to 60 minutes, preferably at 60° C. to 120° C., more preferably at 80° C. to 100° C.

The extract obtained as described above may be used as it is, or as a solution as obtained immediately after the extraction, or as a concentrated extract obtained by purification and concentration of the obtained extract by means of ultrafiltration, centrifugation or the like, or as a powdery extract obtained by further drying the concentrated extract by means of spray drying, freeze drying or the like.

The amount of the above-mentioned extract to be used in the fermented food may preferably be determined after an experimental verification since the resulting effects may differ depending on the species of the bacteria of the genus *Bifidobacterium* and the like. Preferable amount of the extract obtained by water extraction (hereinafter, referred to as "water extraction extract") is about 0.01 to 10% by weight (hereinafter, simply referred to as "%"), more preferably about 0.1% to 5% by weight as calculated in terms of an extract having 10 degrees Brix (sugar content). Preferable amount of the extract obtained by acid extraction (hereinafter, referred to as "acid extraction extract") is 0.001% to 10% by weight, more preferably about 0.01% to 1.0% by weight as calculated in terms of an extract having 10 degrees Brix (sugar content)

In preparation of the fermentation product of the present invention, the water extraction extract or acid extraction extract may be added in an amount greater than 10% or more. However, the viability-improving effects may not be brought about as much as proportional to the amount added. On the contrary, such an excessively large amount of the extract may affect the flavor of the fermented food. It is, therefore, not preferred to add the extract in such an excessively large amount. An amount of water extraction extract smaller than 0.01% or acid extraction extract smaller than 0.001%, on the other hand, may not bring about the viability-improving effects for the bacteria of the genus Bifidobacterium sufficiently and, therefore, is not preferred.

Meanwhile, no particular limitation is imposed on the species of the bacteria of the genus Bifidobacterium, which are used in preparation of the fermentation product of the present invention and are contained in the fermented food, insofar as they are microorganisms belonging to the bacteria of the genus Bifidobacterium. Preferred are those known as the main bacteria of human intestinal flora such as Bifidobacterium breve, Bifidobacterium longum, Bifidobacterium infantis, Bifidobacterium adolescentis, Bifidobacterium bifidum, Bifidobacterium cantenulatum, Bifidobacterium pseudocatenulatum and Bifidobacterium angulatum, the bacteria derived from human intestines such as Bifidobacterium gallicum, the bacteria used in foods such as Bifidobacterium lactis and Bifidobacterium animalis and the like. Among these bacteria of the genus Bifidobacterium, particularly preferred are Bifidobacterium breve, Bifidobacterium bifidum and Bifidobacterium longum in terms of the viability-improving effects obtained when the bacteria are used in combination with the above-described extract(s).

It is possible to obtain the viable-improving effects for the bacteria of the genus Bifidobacterium with the use of extract contained in the fermented food of the present invention even when various microorganisms other than the bacteria of the genus Bifidobacterium are contained in the fermented food. Lactic acid bacteria can be given as an example of other various microorganisms and examples thereof include bacteria of the genus Lactobacillus such as Lactobacillus casei, Lactobacillus acidophilus, Lactobacillus helveticus, Lactobacillus salivarius, Lactobacillus gasseri, Lactobacillus fermentum, Lactobacillus reuteri, Lactobacillus crispatus, Lactobacillus delbrueckii subsp. bulgaricus, Lactobacillus delbueckii subsp. delbueckii and Lactobacillus johnsonii, bacteria of the genus Streptococcus such as Streptococcus thermophilus, bacteria of the genus Lactococcus such as Lactococcus lactis subsp. lactis, Lactococcus lactis subsp. cremoris, Lactococcus plantarum and Lactococcus raffinolactis and bacteria of the genus Enterococcus such as Enterococcus faecalis.

In particular, the viable-improving effects for the bacteria of the genus Bifidobacterium obtained with the use of extract in the fermented food of the present invention can be remarkably exhibited when the cell count of the bacteria of the genus Bifidobacterium contained in the fermented food is $1 \times 10^7$/mL or more, preferably $1 \times 10^8$/mL or more.

The fermented food of the present invention making use of the bacteria of the genus Bifidobacterium (and lactic acid bacteria, as necessary) can be prepared in accordance with a known method for preparing a fermentation product making use of bacteria of the genus Bifidobacterium, except for adding the above-described extract at an arbitrary stage of the preparation procedure. For example, the extract may be added before or after sterilizing a solution containing skim milk powder, followed by inoculation and culture of desired bacteria of the genus Bifidibacterium and the like. The resultant is then homogenized to obtain a fermented milk to serve as a base, followed by addition and mixture of a syrup solution which is separately prepared. Then, flavorings and the like may further be added to prepare a final product. Alternatively, to a sterilized solution containing skim milk powder, desired bacteria of the genus Bifidibacterium and the like is inoculated and cultured. The resultant is homogenized to obtain a fermented milk to serve as a base. Then, a syrup solution which is separately prepared and the above-described extract may be added and mixed thereto, and flavorings and the like may further be added to prepare a final product.

The term "fermented foods" in the present invention includes fermented milks, dairy products, beverages such as lactic acid bacteria beverages, hard yogurt, soft yogurt, plain yogurt and further, kefir, cheese, etc., which are defined by the Ministerial Ordinance concerning Compositional Standards, etc. for Milk and Milk Products. Fermented foods of the present invention, therefore, include various beverages and foods making use of various lactic acid bacteria, for example, fermented milks, lactic acid bacteria beverages, kefir, cheese and the like, which can be of the plain type, flavored type, fruit type, sweetened type, soft type, drink type, solid (hard) type or frozen type.

These fermented foods are obtained by adding thereto a sweetener such as starch syrup and various other food materials, for example, optional ingredients such as various carbohydrates, thickeners, emulsifiers and various vitamins, as needed. Specific examples of these food materials include carbohydrates such as sucrose, glucose, fructose, paratinose, trehalose, lactose, xylose and maltose; glycoalcohols such as sorbitol, xylitol, erythritol, lactitol, palatinate, reduced starch syrup and reduced maltose syrup; sweeteners of high sweetness intensity such as aspartame, thaumatin, sucralose, acesulfame K and stevia; various thickeners (stabilizers) such as agar, gelatin, carrageenan, guar gum, xanthane gum, pectin, locust bean gum, gellan gum, carboxymethylcellulose, soybean polysaccharides and propylene glycol alginate; emulsifiers such as sucrose fatty acid esters, glycerine fatty acid esters, polyglycerine fatty acid esters, sorbitan fatty acid esters and lecithin; milk fats such as cream; butter and sour cream; sours seasonings such as citric acid, lactic acid, acetic acid, malic acid, tartaric acid and gluconic acid; various vitamins such as vitamin A, vitamin Bs, vitamin C and vitamin E; minerals such as calcium, magnesium, zinc, iron and manganese; and flavorings such as yogurt, berry, orange, Chinese quince, perilla, citrus, apple, mint, grape, apricot, pear, custard cream, peach, melon, banana, tropical, herb, black tea and coffee.

In the fermented foods of the present invention which have been described above, the viability of bacteria of the genus Bifidobacterium contained in the foods is improved in storage of the foods by adding and mixing the extracts, compared to that in known fermented foods containing bacteria of the genus Bifidobacterium. Although the reason thereof is not yet clarified, it is assumed that the extracts obtained from each of the plant materials contain large amounts of minerals which contribute to the viability-improving effects for the bacteria of the genus Bifidobacterium.

EXAMPLES

The present invention will hereinafter be described in further detail based on Examples. It should, however, be borne in mind that the present invention is by no means limited to the following examples.

Example 1

Extract Preparation 1

Turmeric (the rootstock of *Curcuma longa* L.), the aerial grass part of *Houttuynia cordata* Thunb., leaves of *Eucommia ulmoides* Oliv., rice bran (a mixture of perocarps, aleurone layers and germs of kernels (brown rice) available from *Oryza Sative* without the chaff paddy), persimmon leaves (leaves of *Diospyros kaki* Thunb.), leaves of *Perilla frutescens* (L.) *Britton* var. acuta *Kudo*, clove (the bud of *Syzygium aromaticum* (L.) Merr. et Perry) and cinnamon (the bark of *Cinnamomum zeylanium* Nees) were each separately subjected to processings such as peeling and crushing, and then extracted for 60 minutes with hot water of 90° C. (in an amount 10 times as much as the weight of the corresponding raw material) to prepare extracts of turmeric, *Houttuynia cordata* Thunb., rice bran, *Eucommia ulmoides* Oliv., persimmon leaves, *perilla*, clove and cinnamon, respectively. The extracts were each separately concentrated to 10 degrees Brix in an evaporator.

The viable cell count of the bacteria in each medium was determined upon completion of culture and after storage at 10° C. for 14 days using TOS medium (product of Yakult Pharmaceutical Ind. Co., Ltd.). Based on the viable cell count thus determined, the viability rate of the bacteria of *Bifidobacterium* was calculated according to the following formula 1. Further, the viability improvement rate in each medium containing the extract was calculated based on the viability rate in the basal medium according to the following formula 2. The results are shown below in Table 1.

$$\text{Viability rate (\%)} = \frac{\text{Viable cell count after storage at } 10° \text{ C. for 14 days}}{\text{Viable cell count upon completion of culture}} \times 100 \quad \text{[Formula 1]}$$

$$\text{Viability improvement rate (\%)} = \left(1 - \frac{100 - \text{Viability rate in medium with addition of extract (\%)}}{100 - \text{Viability rate in basal medium (\%)}}\right) \times 100 \quad \text{[Formula 2]}$$

TABLE 1

| | Basal medium | Turmeric extract | *Houttuynia cordata* Thunb. extract | *Eucommia ulmoides* Oliv. extract | Rice bran extract | Persimmon leaf extract | *Perilla* extract | Clove extract | Cinnamon extract |
|---|---|---|---|---|---|---|---|---|---|
| Viable cell count upon completion of culture (/mL) | $9.2 \times 10^8$ | $9.9 \times 10^8$ | $1.0 \times 10^9$ | $9.7 \times 10^8$ | $1.0 \times 10^9$ | $1.1 \times 10^9$ | $9.1 \times 10^8$ | $8.9 \times 10^9$ | $9.5 \times 10^8$ |
| Viable cell count after storage (/mL) | $5.3 \times 10^8$ | $7.0 \times 10^8$ | $6.8 \times 10^8$ | $7.1 \times 10^8$ | $7.3 \times 10^8$ | $8.3 \times 10^8$ | $6.2 \times 10^8$ | $5.5 \times 10^8$ | $6.1 \times 10^8$ |
| Viability improvement rate (%) | — | 31.0 | 23.8 | 35.7 | 35.7 | 40.1 | 23.8 | 9.5 | 14.3 |

Example 2

Comparison in the Viability of Bacteria of the Genus *Bifidobacterium*

As a basal medium, 12% skim milk powder solution was furnished. The extracts of turmeric, *Houttuynia cordata* Thunb., *Eucommia ulmoides* Oliv., rice bran, persimmon leaves, *perilla*, clove and cinnamon, which had been prepared and adjusted to 10 degrees Brix in Example 1, were added at 1% to aliquots of the basal medium, respectively, followed by sterilization to prepare sterilized media. To each of those media, a starter of *Bifidobacterium breve* strain was inoculated at 1%, and the bacteria strain was cultured at 37° C. until the pH reached about 4.8.

As is clear from Table 1, it has been confirmed that the viability of the bacteria of the genus *Bifidobacterium* improved in a medium with an extract of turmeric, *Houttuynia cordata* Thunb., *Eucommia ulmoides* Oliv., rice bran, persimmon leaves, *perilla*, clove or cinnamon added therein, compared to that in a basal medium.

Example 3

Verification of Effects of Acid Extraction Extract on Viability-Improving Effects for Bacteria of the Genus *Bifidobacterium*

Under similar conditions as in the extract preparation in Example 1 except for the use of water and aqueous solutions, the pHs of which had been adjusted to 3.0, 4.0 and 5.0, respectively, with citric acid instead of hot water, persimmon leaves were treated. To aliquots of a 12% skim milk powder medium, to which the thus-obtained extracts had been added at 1%, respectively, the starter of *Bifidobacterium breve* YIT10001 was inoculated at 1%. The bacteria strain was then cultured at 37° C. until the pH reached about 4.8. The viable cell count of the bacteria in each medium was determined upon completion of culture and after storage of the culture at 10° C. for 14 days in a similar manner as in Example 2. The viability rate and the viability improvement rate were respectively calculated in the same manner as in Example 2. The results are shown below in Table 2.

TABLE 2

|  | Basal medium | Hot water | pH 5.0 | pH 4.0 | pH 3.0 |
|---|---|---|---|---|---|
| Viable cell count upon completion of culture (/mL) | $9.2 \times 10^8$ | $9.5 \times 10^8$ | $9.4 \times 10^8$ | $9.8 \times 10^8$ | $9.6 \times 10^8$ |
| Viable cell count after storage (/mL) | $5.3 \times 10^8$ | $7.0 \times 10^8$ | $7.4 \times 10^8$ | $8.4 \times 10^8$ | $8.3 \times 10^8$ |
| Viability improvement rate (%) | — | 38.1 | 50.0 | 66.7 | 69.0 |

As shown in Table 2, it has been confirmed that the viability-improving effects for the bacteria of the genus *Bifidobacterium* tend to become remarkable with an extract obtained by adjusting the pH of an extraction solvent to 5.0 or less, preferably 4.0 or less.

Example 4

Extract Preparation 2

Turmeric (the rootstock of *Curcuma longa* L.), the aerial grass part of *Houttuynia cordata* Thunb., leaves of *Eucommia ulmoides* Oliv., rice bran (a mixture of perocarps, aleurone layers and germs of kernels (brown rice) available from *Oryza Sative* without the chaff paddy), persimmon leaves (leaves of *Diospyros kaki* Thunb.), leaves of *Perilla frutescens* (L.) Britton var. acuta *Kudo*, clove (the bud of *Syzygium aramaticum* (L.) Merr. et Perry) and cinnamon (the bark of *Cinnamomum zeylanium* Nees), were each separately subjected to processings such as peeling and crushing, and then extracted under similar conditions as in Example 1 except for the use of water and an aqueous solution, the pH of which had been adjusted to pH 4.0 with citric acid, (in amounts 10 times as much as the weight of the corresponding raw material) to prepare extracts of turmeric, *Houttuynia cordata* Thunb., *Eucommia ulmoides* Oliv., rice bran, persimmon leaves, *perilla*, clove and cinnamon, respectively. They were each separately concentrated to 10 degrees Brix, in an evaporator.

Example 5

Verification of Effects of Extract on Viability-Improving Effects for Bacteria of the Genus *Bifidobacterium*

As a basal medium, 15% skim milk powder was furnished. The extract of turmeric, *Houttuynia cordata* Thunb., *Eucommia ulmoides* Oliv., rice bran, persimmon leaves, *perilla*, clove and cinnamon, which had been adjusted to 10 degrees Brix in Example 4, were added at 1% to aliquots of the basal medium to prepare media, respectively. Into each of those media, the starters of various bacteria of the genus *Bifidobacterium* were inoculated at 1%, and those bacteria strains were cultured at 37° C. for 48 hours. The viable cell count of the bacteria in each medium was determined upon completion of culture and after storage of the culture at 10° C. for 14 days in a similar manner as in Example 2. The viability rate and the viability improvement rate were respectively calculated in the same manner as in Example 2. The results are shown below in Table 3.

For the bacteria of the genus *Bifidobacterium* to be cultured, *Bifidobacterium breve* strains, *Bifidobacterium bifidum* strains and *Bifidobacterium longum* strains were used.

TABLE 3

| Bacteria of the genus *Bifidobacterium* | Basal medium | Turmeric extract | *Houttuynia cordata* Thunb. extract | *Eucommia ulmoides* Oliv. extract | Persimmon leaf extract | *Perilla* extract | Clove extract | Cinnamon extract |
|---|---|---|---|---|---|---|---|---|
| *Bifidobacterium Breve* | −(58*) | 60.0 | 52.4 | 57.1 | 66.7 | 54.8 | 50.0 | 47.6 |
| *Bifidobacterium Bifidum* | −(66*) | 65.0 | 67.6 | 55.9 | 70.6 | 44.1 | 55.9 | 50.0 |
| *Bifidobacterium Longum* | −(60*) | 47.5 | 52.4 | 52.4 | 57.1 | 50.0 | 47.5 | 52.5 |

*Viability rate (%)

As is clear from Table 3, the effects of these extracts on the viability of various bacteria of the genus *Bifidobacterium* have been confirmed with substantially all the strains, although they vary depending on the species of the strains. Remarkable effects have been confirmed particularly with the extracts of turmeric, *Houttuynia cordata* Thunb., *Eucommia ulmoides* Oliv. and persimmon leaves.

Example 6

Preparation of Dairy Product 1

A 15% skim milk powder medium was furnished as a basal medium. The various extracts prepared in Example 4 were added at 0.1% to aliquots of the basal medium to provide test media, respectively. After sterilizing those media under heat, the starter of *Bifidobacterium breve* YIT10001 was inoculated at 1%, and the starter of *Lactococcus lactis* YIT2027 and the starter of *Streptococcus thermophilus* YIT2021 were each inoculated at 0.1% to the respective media, and the bacteria strains were cultured at 35° C. for 24 hours to obtain respective cultures. Each culture was homogenized at 15 MPa, and to 40 parts by weight of that culture, 60 parts by weight of a 10% sugar solution, which had been sterilized at 100° C. for 5 minutes, was added, and a yogurt flavoring (product of Yakult Material Co., Ltd.) was further added at 0.1% to prepare a dairy product. A taste test was conducted by five well-experienced assessors on each of the dairy products obtained as descried above. No difference was confirmed between any of the dairy products and the control product which contained the culture obtained with the use of the basal medium.

In addition, the various extracts were assessed to give no flavor-related effects to the basal medium and to match very well. It has, therefore, been also confirmed that their use in cultures for beverages or foods such as dairy products does not lead to deteriorations in their flavors.

Example 7

Effects of Added Amount of Persimmon Leaf Extract on Flavor and Viability-Improving Effects (1) Preparation of Persimmon Leaf Extracts Using water and a solution, the pH of which has been adjusted to 4.0 with citric acid, in amounts of 10 times as much as persimmon leaves, persimmon leaf extracts were prepared under similar conditions as in Example 1. Those extracts were each separately concentrated to 10 degrees Brix in an evaporator.

(2) Determination of an Amount to be Added

To aliquots of a 15% skim milk powder medium, the persimmon leaf extracts prepared above in (1) were added at concentrations in a range of 0.001 to 10%, respectively, followed by sterilization at 100° C. for 60 minutes to prepare media for culturing lactic acid bacteria. To those media, the starter of *Bifidobacterium breve* YIT10001 was inoculated at 1%, and the starter of *Lactococcus lactis* YIT2027 and the starter of *Streptococcus thermophilus* YIT2021 were each inoculated at 0.1%, and the bacteria strains were cultured at 35° C. for 24 hours to obtain respective cultures. Each culture was homogenized at 15 MPa, and to 40 parts by weight of the homogenized culture, 60 parts by weight of a 10% sugar solution, which had been sterilized at 100° C. for 5 minutes, was added, and a yogurt flavoring (product of Yakult Material Co., Ltd.) was further added at 0.1% to prepare a dairy product. With respect to such dairy products, a flavor assessment was conducted by five trained organoleptic assessors based on the following standards. The viable cell count of the bacteria in each medium was determined immediately after preparation of the product and after storage of the product at 10° C. for 14 days in a similar manner as in Example 2. The viability rate and the viability improvement rate were respectively calculated in the same manner as in Example 2. The results are shown in Table 4.

<Assessment Standards>

| (Ranking) | (Description) |
| --- | --- |
| A: | Very good |
| B: | Good |
| C: | Average |
| D: | Poor |
| E: | Very poor |

TABLE 4

| | Added amount of persimmon leaf extract (wt. %) | Cell count of bacteria of the genus *Bifidobacterium* after prepartion (/mL) | Cell count of bacteria of the genus *Bifidobacterium* after storage (/mL) | Viability improvement rate (%) | Flavor assessment |
| --- | --- | --- | --- | --- | --- |
| Basal medium | Not added | $1.2 \times 10^9$ | $3.1 \times 10^8$ | — | A |
| Water extraction | 0.001 | $1.2 \times 10^9$ | $3.2 \times 10^8$ | 1.4 | A |
| | 0.01 | $1.3 \times 10^9$ | $4.2 \times 10^8$ | 8.1 | A |
| | 0.1 | $1.1 \times 10^9$ | $4.4 \times 10^8$ | 18.9 | A |
| | 1 | $1.1 \times 10^9$ | $4.6 \times 10^8$ | 21.6 | B |
| | 5 | $1.2 \times 10^9$ | $4.9 \times 10^8$ | 20.3 | B |
| | 10 | $1.0 \times 10^9$ | $3.8 \times 10^8$ | 16.2 | D |
| Acid extraction (pH 4.0) | 0.001 | $1.2 \times 10^9$ | $3.7 \times 10^8$ | 6.8 | A |
| | 0.01 | $1.1 \times 10^9$ | $4.2 \times 10^8$ | 16.2 | A |
| | 0.1 | $1.2 \times 10^9$ | $5.0 \times 10^8$ | 21.6 | A |
| | 1 | $1.3 \times 10^9$ | $5.2 \times 10^8$ | 18.9 | B |
| | 5 | $1.3 \times 10^9$ | $5.1 \times 10^8$ | 17.6 | B |
| | 10 | $1.1 \times 10^9$ | $4.3 \times 10^8$ | 17.6 | D |

It has been confirmed from Table 4 that the addition of an extract of persimmon leaves at 0.01% or so provides viability-improving effects for the bacteria of the genus *Bifidobacterium*. It has also been ascertained that the addition of an extract of persimmon leaves even as much as 10% to a medium can not bring about any additional excellent effects in proportion to the amounts added, but on the contrary, the flavor derived from the extract tend to affect the flavor of the prepared product. It has also been confirmed that the viability-improving effects of the persimmon leaf extract are exhibited more remarkably with one obtained by acid extraction than with one obtained by water extraction.

Example 8

Effects of Addition Method of Persimmon Leaf Extract on Flavor and Viability-Improving Effects (1) Preparation of Persimmon Leaf Extracts Using water and a solution, the pH of which has been adjusted to 4.0 with citric acid, in amounts of 10 times as much as persimmon leaves, persimmon leaf extracts were prepared under similar conditions as in Example 1. Those extracts were each separately concentrated to 10 degrees Brix in an evaporator.

(2) Determination of Addition Method

A 15% skim milk powder medium was sterilized at 100° C. for 60 minutes to which the starter of *Bifidobacterium breve* YIT10001 was inoculated at 1%, and the starter of *Lactococcus lactis* YIT2027 and the starter of *Streptococcus thermophilus* YIT2021 were each inoculated at 0.1%, and the bacteria strains were cultured at 35° C. for 24 hours to obtain respective cultures. The cell count of lactic acid bacteria in each culture were measured in the similar manner as in Example 2. Each culture was then homogenized at 15 MPa, and to 40 parts by weight of the homogenized culture, 60 parts by weight of a 10% sugar solution, which had been sterilized at 100° C. for 5 minutes, or a solution, which had been obtained by adding and mixing a solution containing the persimmon leaf extracts prepared in above (1) at 0.1% to a 10% sugar solution and sterilizing at 100° C. for 5 minutes, were added, and a yogurt flavoring (product of Yakult Material Co., Ltd.) was further added at 0.1% to prepare a dairy product. With respect to such dairy products, a flavor assessment was conducted by five trained organoleptic assessors based on the standards in Example 7. The viable cell count of the bacteria in each medium was determined immediately after preparation of the product and after storage of the product at 10° C. for 14 days in a similar manner as in Example 2. The viability rate and the viability improvement rate were respectively calculated in the same manner as in Example 2. The results are shown below in Table 5.

ceae), which had been prepared and adjusted to 10 degrees Brix in Example 9, was added at 1% to the basal medium followed by sterilization to prepare a sterilized medium. To that sterilized medium, the starter of *Bifidobacterium breve* strain was inoculated at 1%, and the bacteria strain was cultured at 37° C. until the pH reached about 4.8.

The viable cell count of the bacteria in the medium was determined upon completion of culture and after storage of the culture at 10° C. for 14 days using TOS medium (product of Yakult Pharmaceutical Ind. Co., Ltd.). Based on the viable cell count thus determined, the viability rate of the bacteria of *Bifidobacterium* was calculated according to the following formula 3. Further, the viability improvement rate in the medium containing the extract was calculated based on the viability rate in the basal medium according to the following formula 4. The results are shown below in Table 6.

$$\text{Viability rate } (\%) = \frac{\text{Viable cell count after storage at } 10° \text{ C. for 14 days}}{\text{Viable cell count upon completion of culture}} \times 100 \quad \text{[Formula 3]}$$

$$\text{Viability improvement rate } (\%) = \left(1 - \frac{100 - \text{Viability rate in medium with addition of extract } (\%)}{100 - \text{Viability rate in basal medium } (\%)}\right) \times 100 \quad \text{[Formula 4]}$$

TABLE 5

| Persimmon leaf extract | Cell count of bacteria of the genus *Bifidobacterium* after prepartion (/mL) | Cell count of bacteria of the genus *Bifidobacterium* after storage (/mL) | Viability improvement rate (%) | Flavor assessment |
| --- | --- | --- | --- | --- |
| Not added | $1.2 \times 10^9$ | $3.0 \times 10^8$ | — | A |
| Water extraction | $1.2 \times 10^9$ | $4.2 \times 10^8$ | 13.3 | A |
| Acid extraction (pH 4.0) | $1.3 \times 10^9$ | $4.9 \times 10^8$ | 17.3 | A |

It has been confirmed from Table 5, that viability-improving effects for the bacteria of the genus *Bifidobacterium* are exhibited even when an extract of persimmon leaves is added after culture instead of being added before culture. It is also confirmed that the flavor of a dairy product is not deteriorated even when the extract is added after culture.

Example 9

Extract Preparation 3

Leaves of *Rubus suavissimus* S. Lee (Rosaceae) were subjected to processings such as peeling, crushing and roasting, and then extracted for 60 minutes with hot water of 90° C. (in an amount of 10 times as much as the weight of the leaves of *Rubus suavissimus* S. Lee (Rosaceae)), to prepare an extract of *Rubus suavissimus* S. Lee (Rosaceae). The resultant extract was concentrated to 10 degrees Brix in an evaporator.

Example 10

Verification of the Effects of Extract for Bacteria of the Genus *Bifidobacterium*

As a basal medium, a 12% skim milk powder solution was furnished. The extract of *Rubus suavissimus* S. Lee (Rosa-

TABLE 6

|  | Basal medium | *Rubus suavissimus* S. Lee (Rosaceae) Extract |
| --- | --- | --- |
| Viable cell count upon completion of culture(/mL) | $1.2 \times 10^9$ | $1.2 \times 10^9$ |
| Viable cell count after storage (/mL) | $6.1 \times 10^8$ | $7.8 \times 10^8$ |
| Viability improvement rate (%) | — | 40.8 |

As confirmed from Table 6, a medium added with an extract of *Rubus suavissimus* S. Lee (Rosaceae) provides better viability-improving effects for the bacteria of the genus *Bifidobacterium* compared to a basal medium.

Example 11

Verification of Acid Extraction Extract 1

Under similar conditions as in the extract preparation in Example 9 except for the use of water and aqueous solutions, the pHs of which had been adjusted to 3.0, 4.0 and 5.0, respectively, with citric acid instead of hot water, *Rubus suavissimus* S. Lee (Rosaceae) was treated. To aliquots of a 12% skim milk powder medium, to which the thus-obtained extracts had been added at 1%, respectively, the starter of

*Bifidobacterium breve* YIT10001 was inoculated at 1%. The bacteria strain was then cultured at 37° C. until the pH reached about 4.8. The viable cell count of the bacteria in each medium was determined upon completion of culture and after storage of the culture at 10° C. for 14 days in a similar manner as in Example 10. The viability rate and the viability improvement rate were respectively calculated in the same manner as in Example 10. The results are shown below in Table 7.

TABLE 7

|  | Basal medium | Hot water | pH 5.0 | pH 4.0 | pH 3.0 |
|---|---|---|---|---|---|
| Viable cell count upon completion of culture (/mL) | $1.2 \times 10^9$ | $1.2 \times 10^9$ | $1.1 \times 10^9$ | $1.2 \times 10^9$ | $1.2 \times 10^9$ |
| Viable cell count after storage (/mL) | $6.1 \times 10^8$ | $7.8 \times 10^8$ | $7.6 \times 10^8$ | $8.8 \times 10^8$ | $8.9 \times 10^8$ |
| Viability improvement rate (%) | — | 29 | 37 | 45 | 47 |

It is confirmed from Table 7 that the viability improving effects for the bacteria of the genus *Bifidobacterium* tends to be remarkable when using a solvent added with an extract of *Rubus suavissimus* S. Lee (Rosaceae) has higher pH.

Example 12

Extract Preparation 4

Leaves of *Rubus suavissimus* S. Lee (Rosaceae) were subjected to processings such as peeling, crushing and roasting, and then extracted under similar conditions as in Example 9 with an aqueous solution of citric acid adjusted to pH 4.0 (in an amount of 10 times as much as the weight of the leaves of *Rubus suavissimus* S. Lee (Rosaceae)) to prepare an extract of *Rubus suavissimus* S. Lee (Rosaceae). The thus-obtained extract was concentrated to 10 degrees Brix in an evaporator.

Example 13

Verification of Acid Extraction Extract 2

As a basal medium, 15% skim milk powder medium was furnished. The extract of *Rubus suavissimus* S. Lee (Rosaceae), which had been adjusted to 10 degrees Brix in Example 12, were added at 1.0% to aliquots of the basal medium to prepare media, respectively. Into each of those media, the starters of various bacteria of the genus *Bifidobacterium* were inoculated at 1%, and those bacteria strains were cultured at 37° C. until the pH reached about 4. The viable cell count of the bacteria in each medium was determined upon completion of culture and after storage of the culture at 10° C. for 14 days in a similar manner as in Example 10. The viability rate and the viability improvement rate were respectively calculated in the same manner as in Example 10. The results are shown below in Table 8.

For the bacteria of the genus *Bifidobacterium* to be cultured, *Bifidobacterium breve* strains, *Bifidobacterium bifidum* strains and *Bifidobacterium longum* strains were used.

TABLE 8

| | Basal medium | | | | Extract of *Rubus suavissimus* S. Lee (Rosaceae) | | | |
|---|---|---|---|---|---|---|---|---|
| Bacteria of the genus *Bifidobacterium* | Viable cell count upon completion of culture (/mL) | Viable cell count after storage (/mL) | Viability improvement rate (%) | Culture time (hrs) | Viable cell count upon completion of culture (/mL) | Viable cell count after storage (/mL) | Viability improvement rate (%) | Culture time (hrs) |
| *Bifidobacterium Breve* | $1.2 \times 10^9$ | $6.1 \times 10^8$ | — | 41 | $1.1 \times 10^9$ | $8.1 \times 10^8$ | 47 | 40 |
| *Bifidobacterium Bifidum* | $1.0 \times 10^9$ | $4.8 \times 10^8$ | — | 48 | $1.2 \times 10^9$ | $9.8 \times 10^8$ | 65 | 44 |
| *Bifidobacterium Longum* | $1.1 \times 10^9$ | $5.6 \times 10^8$ | — | 45 | $1.2 \times 10^9$ | $8.4 \times 10^8$ | 39 | 44 |

As is clear from Table 8, the effects of *Rubus suavissimus* S. Lee (Rosaceae) extract on the viability improvement of the bacteria of the genus *Bifidobacterium* have been confirmed with substantially all the strains, although they vary depending on the species of the strains. There was also confirmed an effect that with some of the strains, the culture time was shortened.

Example 14

Preparation of Dairy Product 2

A 20% skim milk powder medium was furnished as a basal medium. The extract of *Rubus suavissimus* S. Lee (Rosaceae) prepared in Example 12 was added at 0.1% to aliquots of the basal medium to provide test media, respectively. After sterilizing those media under heat, the starter of *Bifidobacterium breve* YIT10001 was inoculated at 1%, and the starter of *Lactococcus lactis* YIT2027 and the starter of *Streptococcus thermophilus* YIT2021 were each inoculated at 0.1% to the respective media, and the bacteria strains were cultured at 35° C. for 24 hours to obtain respective cultures. Each culture was homogenized at 15 MPa, and to 40 parts by weight of that culture, 60 parts by weight of a 10% sugar solution, which had been sterilized at 100° C. for 5 minutes, was added, and a yogurt flavoring (product of Yakult Material Co., Ltd.) was further added at 0.1% to prepare a dairy product. A taste test was conducted by five well-experienced assessors on each of the dairy products obtained as descried above. No difference was confirmed between any of the dairy products and the control product which contained the culture obtained with the use of the basal medium.

In addition, the extract of *Rubus suavissimus* S. Lee (Rosaceae) was assessed to give no flavor-related effects to the basal medium and to match very well. It has, therefore, been also confirmed that its use in cultures for beverages or foods such as dairy products does not lead to deteriorations in their flavors.

Example 15

Effects of Added Amount of *Rubus suavissimus* S. Lee (Rosaceae) Extract on Flavor, Proliferativeness and Viability-Improving Effects (1) Preparation of *Rubus suavissimus* S. Lee (Rosaceae) Extracts Using water and a solution, the pH of which has been adjusted to 4.0 with citric acid, in amounts of 10 times as much as *Rubus suavissimus* S. Lee (Rosaceae), *Rubus suavissimus* S. Lee (Rosaceae) extracts were prepared under similar conditions as in Example 9. Those extracts were each separately concentrated to 10 degrees Brix in an evaporator.

(2) Determination of an Amount to be Added

To aliquots of a 20% skim milk powder medium, *Rubus suavissimus* S. Lee (Rosaceae) extracts prepared above in (1) were added at concentrations in a range of 0.001 to 10%, respectively, followed by sterilization at 100° C. for 60 minutes to prepare culture media. To those media, the starter of *Bifidobacterium breve* YIT10001 was inoculated at 1%, and the starter of *Lactococcus lactis* YIT2027 and the starter of *Streptococcus thermophilus* YIT2021 were each inoculated at 0.1%, and the bacteria strains were cultured at 35° C. for 24 hours to obtain respective cultures. The cell count of the lactic acid bacteria in each culture was measured in a similar manner as in Example 10. Each culture was homogenized at 15 MPa, and to 40 parts by weight of the homogenized culture, 60 parts by weight of a 10% sugar solution, which had been sterilized at 100° C. for 5 minutes, was added, and a yogurt flavoring (product of Yakult Material Co., Ltd.) was further added at 0.1% to prepare a dairy product. With respect to such dairy products, a flavor assessment was conducted by five trained organoleptic assessors based on the following standards. The viable cell count of the bacteria in each medium was determined immediately after preparation of the product and after storage of the product at 10° C. for 14 days in a similar manner as in Example 10. The viability rate and the viability improvement rate were respectively calculated in the same manner as in Example 10. The results are shown in Table 9.

<Assessment Standards>

| (Ranking) | (Description) |
|---|---|
| A: | Very good |
| B: | Good |
| C: | Average |
| D: | Poor |
| E: | Very poor |

TABLE 9

| | Added amount of *Rubus suavissimus* S. Lee (Rosaceae) (wt. %) | Cell count of bacteria of the genus *Bifidobacterium* after prepartion (/mL) | Cell count of bacteria of the genus *Bifidobacterium* after storage (/mL) | Viability improvement rate (%) | Flavor |
|---|---|---|---|---|---|
| Basal medium | Not added | $1.3 \times 10^9$ | $3.1 \times 10^8$ | — | A |
| Hot water-extraction | 0.001 | $1.2 \times 10^9$ | $3.3 \times 10^8$ | 5 | A |
| | 0.01 | $1.3 \times 10^9$ | $4.5 \times 10^8$ | 14 | A |
| | 0.1 | $1.4 \times 10^9$ | $4.9 \times 10^8$ | 15 | A |
| | 1 | $1.3 \times 10^9$ | $4.9 \times 10^8$ | 18 | B |
| | 5 | $1.2 \times 10^9$ | $5.1 \times 10^8$ | 24 | C |
| | 10 | $1.2 \times 10^9$ | $4.3 \times 10^8$ | 16 | D |
| Acid extraction (pH 4.0) | 0.001 | $1.2 \times 10^9$ | $3.7 \times 10^8$ | 9 | A |
| | 0.01 | $1.2 \times 10^9$ | $4.5 \times 10^8$ | 18 | A |
| | 0.1 | $1.2 \times 10^9$ | $5.3 \times 10^8$ | 27 | A |
| | 1 | $1.3 \times 10^9$ | $5.6 \times 10^8$ | 25 | B |
| | 5 | $1.3 \times 10^9$ | $5.6 \times 10^8$ | 25 | C |
| | 10 | $1.2 \times 10^9$ | $4.8 \times 10^8$ | 21 | D |

It has been confirmed from Table 9 that the addition of an extract of *Rubus suavissimus* S. Lee (Rosaceae) at 0.01% or so provides viability-improving effects for the bacteria of the genus *Bifidobacterium*. It has also been ascertained that the addition of an extract of *Rubus suavissimus* S. Lee (Rosaceae) even as much as 10% to a medium can not bring about any additional excellent effects in proportion to the amounts added, but on the contrary, the flavor of the prepared product was affected. It has also been confirmed that the viability-improving effects of the *Rubus suavissimus* S. Lee (Rosaceae) extract are exhibited more remarkably with one obtained by acid extraction than with one obtained by hot water extraction.

Example 16

Verification of Effects of Addition Method of *Rubus suavissimus* S. Lee (Rosaceae) Extract on Viability Improvement for Bacteria of the Genus *Bifidobacterium*

(1) Preparation of *Rubus suavissimus* S. Lee (Rosaceae) Extracts

Using water and a solution, the pH of which has been adjusted to 4.0 with citric acid, in amounts of 10 times as much as *Rubus suavissimus* S. Lee (Rosaceae), *Rubus suavissimus* S. Lee (Rosaceae) extracts were prepared under similar conditions as in Example 9. Those extracts were each separately concentrated to 10 degrees Brix in an evaporator.

(2) Determination of Addition Method

A 20% skim milk powder medium was sterilized at 100° C. for 60 minutes to which the starter of *Bifidobacterium breve* YIT10001 was inoculated at 1%, and the starter of *Lactococcus lactis* YIT2027 and the starter of *Streptococcus thermophilus* YIT2021 were each inoculated at 0.1%, and the bacteria strains were cultured at 35° C. for 24 hours to obtain respective cultures. Each culture was then homogenized at 15 MPa, and to 40 parts by weight of the homogenized culture, 60 parts by weight of a 10% sugar solution, which had been sterilized at 100° C. for 5 minutes, or a solution, which had been obtained by adding and mixing a solution containing the persimmon leaf extracts prepared in above (1) at 0.1% to a 10% sugar solution and sterilizing at 100° C. for 5 minutes, were added, and a yogurt flavoring (product of Yakult Material Co., Ltd.) was further added at 0.1% to prepare a dairy product. With respect to such dairy products, the viable cell count of the bacteria in each medium was determined upon completion of culture and after storage at 10° C. for 14 days in a similar manner as in Example 2. The viability rate and the viability improvement rate were respectively calculated in the same manner as in Example 10. The results are shown below in Table 10.

TABLE 10

| *Rubus suavissimus* S. Lee (Rosaceae) extract | Cell count of bacteria of the genus *Bifidobacterium* after prepartion (/mL) | Cell count of bacteria of the genus *Bifidobacterium* after storage (/mL) | Viability improvement rate (%) |
|---|---|---|---|
| Not added | $1.3 \times 10^9$ | $3.1 \times 10^8$ | — |
| Hot water extraction | $1.2 \times 10^9$ | $4.0 \times 10^8$ | 12 |
| Acid extraction (pH 4.0) | $1.3 \times 10^9$ | $4.8 \times 10^8$ | 17 |

As it can been understood from Table 10, the viability-improving effects for the bacteria of the genus *Bifidobacterium* provided with the use of *Rubus suavissimus* S. Lee (Rosaceae) extract can be exhibited irrespective of the timing of addition of the extract.

INDUSTRIAL APPLICABILITY

The fermented food of the present invention contains bacteria of the genus *Bifidobacterium* while undergoing not much deteriorations in flavor and maintaining the cell count of the bacteria even after storage of the food for a long period of time. Accordingly, this fermented product can be suitably used in the promotion of health.

The invention claimed is:

1. A method for producing a fermented food containing live bifidobacteria comprising:
   including in a fermented food that contains live bifidobacteria an acid extraction extract of *Rubus suavissimus* S. Lee (Rosaceae);
   wherein said acid extraction extract is prepared by extracting said *Rabus suavissimus* S. Lee (Rosaceae) in an aqueous acid solution at pH 4.0 or less;
   wherein said acid extraction extract is included in an amount ranging from 0.001% 1.0% by weight as calculated in terms of an extract adjusted to 10 degrees Brix (sugar content);
   wherein said extract is included in an amount sufficient to increase the viability of the bifidobacteria in the fermented food after storage at 10° C. for 14 days compared to the viability of bifidobacteria in an otherwise identical fermented food which does not contain the extract; and
   wherein said bifidobacteria are selected from the group consisting of *Bifidobacterium breve* and *Bifidobacterium bifidum*; or both.

2. The method of claim 1, wherein said live bifidobacteria are *Bifidobacterium breve*.

3. The method of claim 1, wherein said fermented food contains $1 \times 10^7$/mL or more live bifidobacteria.

4. The method of claim 1, wherein said fermented food contains $1 \times 10^8$/mL or more live bifidobacteria.

5. The method of claim 1, wherein the fermented food is a fermented milk or dairy product.

6. The method of claim 5, wherein the fermented milk or dairy product is selected from the group consisting of a fermented milk, hard yogurt, soft yogurt, and plain yogurt.

7. The method of claim 5, wherein the fermented food is kefir or cheese.

8. The method of claim 1, wherein said acid extraction extract is an extract of *Rubus suavissimus* S. Lee (Rosaceae) leaves prepared by extraction in an aqueous solution of citric acid.

9. The method of claim 8, wherein the fermented food is a fermented milk or dairy product.

10. The method of claim 8, wherein the acid extraction extract is added to a fermented milk or fermented dairy product selected from the group consisting of a fermented milk, hard yogurt, soft yogurt, plain yogurt, kefir and cheese.

11. A fermented food produced by the method of claim 1.
12. A fermented food produced by the method of claim 2.
13. A fermented food produced by the method of claim 3.
14. A fermented food produced by the method of claim 4.
15. A fermented food produced by the method of claim 5.
16. A fermented food produced by the method of claim 6.
17. A fermented food produced by the method of claim 7.
18. A fermented food produced by the method of claim 8.
19. A fermented food produced by the method of claim 9.
20. A fermented food produced by the method of claim 10.

21. A fermented milk food containing live bifidobacteria comprising an acid extraction extract of at least one plant material selected from the group consisting of turmeric (rootstock of *Curcuma longa* L.), *Houttuynia cordata* Thunb., *Eucommia ulmoides* Oliv., rice bran, persimmon leaves, clove, cinnamon, and *Rubus suavissimus* S. Lee (Rosaceae);
   wherein said acid extraction extract is prepared by extracting said at least one plant material in an aqueous acid solution at pH 4.0 or less;
   wherein said acid extraction extract is included in an amount ranging from 0.001% 10.0% by weight of the fermented milk food as calculated in terms of an extract adjusted to 10 degrees Brix (sugar content); and wherein said extract is included in an amount sufficient to increase the viability of the bifidobacteria in the fermented milk food after storage at 10° C. for 14 days compared to the viability of bifidobacteria in an otherwise identical fermented milk food which does not contain the extract.

22. A fermented food produced by the method of claim 21.

* * * * *